US008198055B2

(12) United States Patent
Datta et al.

(10) Patent No.: US 8,198,055 B2
(45) Date of Patent: *Jun. 12, 2012

(54) PROCESS FOR CONVERTING SYNGAS TO LIQUID PRODUCTS WITH MICROORGANISMS ON TWO-LAYER MEMBRANE

(75) Inventors: Rathin Datta, Chicago, IL (US); Shih-Perng Tsai, Naperville, IL (US); Rahul Basu, Naperville, IL (US); Seong-Hoon Yoon, Naperville, IL (US)

(73) Assignee: Coskata, Inc., Warrenville, IL (US)

( * ) Notice: Subject to any disclaimer, the term of this patent is extended or adjusted under 35 U.S.C. 154(b) by 754 days.

This patent is subject to a terminal disclaimer.

(21) Appl. No.: 12/205,540

(22) Filed: Sep. 5, 2008

(65) Prior Publication Data
US 2009/0017514 A1 Jan. 15, 2009

Related U.S. Application Data

(63) Continuation-in-part of application No. 11/781,717, filed on Jul. 23, 2007, now abandoned.

(60) Provisional application No. 60/942,938, filed on Jun. 8, 2007.

(51) Int. Cl.
| C12P 7/54 | (2006.01) |
| C12P 7/40 | (2006.01) |
| C12P 7/52 | (2006.01) |
| C12P 7/30 | (2006.01) |
| C12P 7/04 | (2006.01) |
| C12P 7/16 | (2006.01) |
| C12P 7/06 | (2006.01) |
| C12M 1/00 | (2006.01) |
| C12M 1/12 | (2006.01) |

(52) U.S. Cl. ........ 435/140; 435/136; 435/141; 435/154; 435/157; 435/160; 435/161; 435/289.1; 435/297.1; 435/297.2; 435/297.4

(58) Field of Classification Search .................. None
See application file for complete search history.

(56) References Cited

U.S. PATENT DOCUMENTS

| 4,181,604 | A | | 1/1980 | Onishi et al. |
| 4,377,638 | A | * | 3/1983 | Bryant et al. ................ 435/136 |
| 4,440,853 | A | | 4/1984 | Michaels et al. |
| 4,442,206 | A | | 4/1984 | Michaels et al. |
| 4,746,435 | A | | 5/1988 | Onishi et al. |
| 5,116,506 | A | * | 5/1992 | Williamson et al. .......... 210/610 |
| 5,173,429 | A | | 12/1992 | Gaddy et al. |
| 5,702,503 | A | * | 12/1997 | Tse Tang ........................ 95/45 |
| 5,753,474 | A | | 5/1998 | Ramey |
| 5,821,111 | A | | 10/1998 | Grady et al. |
| 5,954,858 | A | * | 9/1999 | Peretti et al. ...................... 95/44 |
| 6,043,392 | A | | 3/2000 | Holtzapple et al. |
| 6,136,577 | A | | 10/2000 | Gaddy |
| 6,340,581 | B1 | | 1/2002 | Gaddy |
| 6,387,262 | B1 | | 5/2002 | Rittmann et al. |
| 6,558,549 | B2 | | 5/2003 | Cote et al. |
| 6,723,886 | B2 | * | 4/2004 | Allison et al. ................ 568/909 |
| 6,844,187 | B1 | * | 1/2005 | Wechsler et al. .......... 435/297.2 |
| 6,908,547 | B2 | | 6/2005 | Cote et al. |
| 6,919,488 | B2 | | 7/2005 | Melnichuk et al. |
| 7,118,672 | B2 | | 10/2006 | Husain et al. |
| 7,169,295 | B2 | | 1/2007 | Husain et al. |
| 7,175,763 | B2 | | 2/2007 | Husain et al. |
| 7,189,323 | B2 | | 3/2007 | Lofqvist et al. |
| 7,285,402 | B2 | | 10/2007 | Gaddy et al. |
| 7,294,259 | B2 | | 11/2007 | Cote et al. |
| 7,300,571 | B2 | | 11/2007 | Cote et al. |
| 7,303,677 | B2 | | 12/2007 | Cote et al. |
| 7,704,723 | B2 | | 4/2010 | Huhnke et al. |
| 7,732,173 | B2 | * | 6/2010 | Mairal et al. .................... 435/161 |
| 7,923,227 | B2 | * | 4/2011 | Hickey et al. ................. 435/161 |
| 2004/0065607 | A1 | * | 4/2004 | Wang et al. .............. 210/500.41 |
| 2006/0037896 | A1 | * | 2/2006 | Cote et al. ..................... 210/150 |
| 2007/0275447 | A1 | | 11/2007 | Lewis et al. |
| 2008/0305539 | A1 | | 12/2008 | Hickey et al. |
| 2008/0305540 | A1 | | 12/2008 | Hickey et al. |
| 2009/0029434 | A1 | | 1/2009 | Tsai et al. |
| 2009/0035848 | A1 | | 2/2009 | Hickey et al. |
| 2009/0104676 | A1 | | 4/2009 | Tsai et al. |
| 2009/0215139 | A1 | | 8/2009 | Datta et al. |
| 2009/0215142 | A1 | | 8/2009 | Tsai et al. |
| 2009/0215153 | A1 | | 8/2009 | Tsai et al. |
| 2009/0286296 | A1 | | 11/2009 | Hickey et al. |
| 2010/0105116 | A1 | | 4/2010 | Datta et al. |

FOREIGN PATENT DOCUMENTS

| WO | WO9800558 A1 | 1/1998 |
| WO | WO 02/08438 | 1/2002 |
| WO | WO2008154301 A1 | 12/2008 |

OTHER PUBLICATIONS

Clausen, E.C., et al., "Ethanol From Biomass by Gasification/Fermentation", Presented at Plastics, Tires, Auto Wastes/Biomass MSW Symposium, Fall 1993, Chicago, 38 (3).

Klasson, K.T., et al., "Biological Production of Liquid and Gaseous Fuels from Synthesis Gas," Appl. Biochem. Biotechnol., vol. 24-25, No. 1, Mar. 1990, 857-873.

Vega, J. L., et al., "The Biological Production of Ethanol from Synthesis Gas," Appl. Biochem. Biotechnol. vol. 20-21, No. 1, Jan. 1989, 781-797.

Phillips, John R., et al., "Synthesis Gas as Substrate for the Biological Production of Fuels and Chemicals," Appl. Biochem. Biotechnol. vol. 45-46, No. 1, Mar. 1994, 145-157.

(Continued)

*Primary Examiner* — David Naff
(74) *Attorney, Agent, or Firm* — Cardinal Law Group

(57) ABSTRACT

Ethanol and other liquid products are produced by contacting syngas components such as CO or a mixture of $CO_2$ and $H_2$ with a surface of a membrane under anaerobic conditions and transferring these components in contact with a biofilm on the opposite side of the membrane. These steps provide a stable system for producing liquid products such as ethanol, butanol and other chemicals. The gas fed on the membrane's gas contact side transports through the membrane to form a biofilm of anaerobic microorganisms that converted the syngas to desired liquid products. A liquid impermeable layer of the membrane assists in establishing direct gas phase contact syngas components with the microorganisms. The system can sustain production with a variety of microorganisms and membrane configurations.

8 Claims, 5 Drawing Sheets

OTHER PUBLICATIONS

Barik, S., et al., "Biological Production of Alcohols from Coal Through Indirect Liquefaction," Appl. Biochem. Biotechnol. vol. 18, No. 1, Aug. 1988, 363-387.

Popular Mechanics, Coskata Ethanol Technology—How it Works—Illustration and Analysis, http://www.popularmechanics.com/science/research/4248759.html?series=19, Feb. 22, 2008, pp. 1-3.

Ethanol Production by *Saccharomyces cerevisiae* Immobilized in Hollow-Fiber Membrane Bioreactors, Douglas S. Inloes, et al., Applied and Environmental Microbiology, Jul. 1983, pp. 264-278, vol. 46. No. 1.

"Evidence for Production of n-Butanol from Carbon Monoxide by *Butyribacterium methylotrophicum*," Journal of Fermentation and Bioengineering, vol. 72, 1991, p. 58-60.

"Production of butanol and ethanol from synthesis gas via fermentation," FUEL, vol. 70, May 1991, p. 615-619.

Das, A. and L.G. Ljungdahl, Electron Transport Systems in Acetogens, Chapter 14, in Biochemistry and Physiology of Anaerobic Bacteria, L.G. Ljungdahl et al eds., Springer (2003).

Drake, H.L. and K. Kusel, Diverse Physiologic Potential of Acetogens, Chapter 13, in Biochemistry and Physiology of Anaerobic Bacteria, L.G. Ljungdahl et al eds., Springer (2003).

Muller, V., Minireview: Energy Conservation in Acetogenic Bacteria, Applied and Environmental Microbiology, vol. 69, 11, 6345-53, Nov. 2003.

Innovations in Wastewater Treatment: The moving bed biofilm process. Water Science and Technology vol. 53 No. 9 pp. 17-33.

Rathin Datta and J.G. Zeikus, Anaerobic Conversion of One-Carbon Compounds. vol. 24 of Developments in Industrial Microbiology, 1983.

\* cited by examiner

PROCESS FOR CONVERTING SYNGAS TO LIQUID PRODUCTS WITH MICROORGANISMS ON TWO-LAYER MEMBRANE

CROSS REFERENCE TO RELATED APPLICATIONS

This application is a continuation in part of U.S. application Ser. No. 11/781,717 filed Jul. 23, 2007, now abandoned which is an application claiming benefit under 35 USC 119(c) of U.S. Provisional Patent Application Ser. No. 60/942,938 filed Jun. 8, 2007.

FIELD OF THE INVENTION

This invention relates to the biological conversion of CO and mixtures of $CO_2$ and $H_2$ to liquid products.

DETAILED DESCRIPTION

Background

Biofuels production for use as liquid motor fuels or for blending with conventional gasoline or diesel motor fuels is increasing worldwide. Such biofuels include, for example, ethanol and n-butanol. One of the major drivers for biofuels is their derivation from renewable resources by fermentation and bioprocess technology. Conventionally, biofuels are made from readily fermentable carbohydrates such as sugars and starches. For example, the two primary agricultural crops that are used for conventional bioethanol production are sugarcane (Brazil and other tropical countries) and corn or maize (U.S. and other temperate countries). The availability of agricultural feedstocks that provide readily fermentable carbohydrates is limited because of competition with food and feed production, arable land usage, water availability, and other factors. Consequently, lignocellulosic feedstocks such as forest residues, trees from plantations, straws, grasses and other agricultural residues may become viable feedstocks for biofuel production. However, the very heterogeneous nature of lignocellulosic materials that enables them to provide the mechanical support structure of the plants and trees makes them inherently recalcitrant to bioconversion. Also, these materials predominantly contain three separate classes of components as building blocks: cellulose ($C_6$ sugar polymers), hemicellulose (various $C_5$ and $C_6$ sugar polymers), and lignin (aromatic and ether linked hetero polymers).

For example, breaking down these recalcitrant structures to provide fermentable sugars for bioconversion to ethanol typically requires pretreatment steps together with chemical/enzymatic hydrolysis. Furthermore, conventional yeasts are unable to ferment the $C_5$ sugars to ethanol and lignin components are completely unfermentable by such organisms. Often lignin accounts for 25 to 30% of the mass content and 35 to 45% of the chemical energy content of lignocellulosic biomass. For all of these reasons, processes based on a pretreatment/hydrolysis/fermentation path for conversion of lignocellulose biomass to ethanol, for example, are inherently difficult and often uneconomical multi-step and multi conversion processes.

An alternative technology path is to convert lignocellulosic biomass to syngas (also known as synthesis gas, primarily a mix of CO, $H_2$ and $CO_2$ with other components such as $CH_4$, $N_2$, $NH_3$, $H_2S$ and other trace gases) and then ferment this gas with anaerobic microorganisms to produce biofuels such as ethanol, n-butanol or chemicals such as acetic acid, butyric acid and the like. This path can be inherently more efficient than the pretreatment/hydrolysis/fermentation path because the gasification step can convert all of the components to syngas with good efficiency (e.g., greater than 75%), and some strains of anaerobic microorganisms can convert syngas to ethanol, n-butanol or other chemicals with high (e.g., greater than 90% of theoretical) efficiency. Moreover, syngas can be made from many other carbonaceous feedstocks such as natural gas, reformed gas, peat, petroleum coke, coal, solid waste and land fill gas, making this a more universal technology path.

However, this technology path requires that the syngas components CO and $H_2$ be efficiently and economically dissolved in the aqueous medium and transferred to anaerobic microorganisms that convert them to the desired products. And very large quantities of these gases are required. For example, the theoretical equations for CO or $H_2$ to ethanol are:

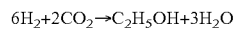

Thus 6 moles of relatively insoluble gases such as CO or $H_2$ have to transfer to an aqueous medium for each mole of ethanol. Other products such as acetic acid and n-butanol have similar large stoichiometric requirements for the gases. Furthermore, the anaerobic microorganisms that bring about these bioconversions generate very little metabolic energy from these bioconversions. Consequently they grow very slowly and often continue the conversions during the non-growth phase of their life cycle to gain metabolic energy for their maintenance.

Many devices and equipment are used for gas transfer to microorganisms in fermentation and waste treatment applications. These numerous bioreactors all suffer from various drawbacks. In most of these conventional bioreactors and systems, agitators with specialized blades or configurations are used. In some others such as gas lift or fluidized beds, liquids or gases are circulated via contacting devices. The agitated vessels require a lot of mechanical power often in the range of 4 to 10 KW per 1000 gallons—uneconomical and unwieldy for large scale fermentations that will be required for such syngas bioconversions. The fluidized or fluid circulating systems cannot provide the required gas dissolution rates. Furthermore, most of these reactors or systems are configured for use with microorganisms in planktonic form i.e. they exist as individual cells in liquid medium.

Furthermore, to get high yields and production rates the cell concentrations in the bioreactor need to be high and this requires some form of cell recycle or retention. Conventionally, this is achieved by filtration of the fermentation broth through microporous or nonporous membranes, returning the cells and purging the excess. These systems are expensive and require extensive maintenance and cleaning of the membranes to maintain the fluxes and other performance parameters.

Cell retention by formation of biofilms is a very good and often inexpensive way to increase the density of microorganisms in bioreactors. This requires a solid matrix with large surface area for the cells to colonize and form a biofilm that contains the metabolizing cells in a matrix of biopolymers that the cells generate. Trickle bed and some fluidized bed bioreactors make use of biofilms to retain microbial cells on solid surfaces while providing dissolved gases in the liquid by flow past the solid matrix. They suffer from either being very large or unable to provide sufficient gas dissolution rates.

Particular forms of membranes have found use in supporting specific types of microorganisms for waste water treatment processes. U.S. Pat. No. 4,181,604 discloses the use of hollow fiber membranes for waste treatment where the outer surface of the fibers supports a layer of microorganisms for aerobic digestion of sludge.

Existing commercially available membranes of the various geometries and compositions described above may be used in arrangements of unitary arrays or assemblies of varied composition in membrane supported biofilm bioreactors for conversion of syngas components to liquid products. However, there remains a need for a bioreactor membrane system that can easily manage the gas-liquid interface and provide high flux of CO and $H_2$ transfer over extended operations in large scale plants. Microporous membranes require very precise control of the pressure difference across the membrane to maintain the desired gas-liquid interface. Existing composite and dense membranes have limited flux for CO and $H_2$ transfer due to low permeability of the membrane of the non-porous layer or long diffusion path (especially for the dense membrane).

SUMMARY OF THE INVENTION

It has been found that contacting syngas components such as CO or a mixture of $CO_2$ and $H_2$ with a liquid impermeable surface of a membrane and transferring these components into contact with a biofilm on a microporous surface of the membrane will provide a stable system for producing liquid products such as ethanol, butanol and other chemicals. Accordingly this invention is a membrane supported bioreactor system for conversion of syngas components such as CO, $CO_2$ and $H_2$ to liquid fuels and chemicals by passing the syngas components across a liquid impermeable surface into contact with anaerobic microoganisms supported on a microporous surface of the membrane. The gas fed on the membrane's gas contact side transports through the membrane to a biofilm of the anaerobic microorganisms where it is converted to the desired liquid products.

The instant invention uses a combination of a microporous membrane surface with a liquid impermeable surface that transfers gases into contact with microorganisms present in and about one of the membrane surfaces. This invention uses a combination of a microporous membrane layer and a liquid impermeable layer to provide a biofilm support and to transfer gases into direct gas phase contact with microorganisms that consume the gas in the production of liquid products. Contact with the microorganisms converts the delivered syngas into ethanol and other liquid soluble products. The liquid impermeable layer of the membrane assists in establishing direct gas phase contact of syngas components with the microorganisms. Using the liquid impermeable layer reduces or eliminates the leakage of water and water and hydrophilic liquids in to the pores of the membranes that otherwise can limit, sometimes severely, the mass transfer rate of the feed components into the microorganisms and any resulting biofilm. The result is a highly efficient and economical transfer of the syngas at essentially 100% dissolution and utilization, overcoming limitations for the other fermentation methods and fermenter configurations. The syngas diffuses through the liquid impermeable portion of the membrane from the gas side and into the biofilm where it is transformed by the microbes to the soluble product of interest. Liquid is passed in the liquid side of the membranes via pumping, stirring or similar means to remove the ethanol and other soluble products formed; the products are recovered via a variety of suitable methods.

A broad embodiment of this invention is a bioreactor membrane system for converting a feed gas to a liquid product. The system includes a bio-support membrane having a microporous layer and a liquid impermeable layer with one side of each layer defining opposing inner faces and the opposite side of each layer defining an outer face. The outer face of the microporous layer provides a biofilm support side for maintaining a biofilm containing a microorganism that produces the liquid product. The outer face of the liquid impermeable layer provides a gas contacting side in contact with the feed gas for transferring said feed gas across the liquid impermeable layer. A liquid retention chamber establishes fluid communication with the biofilm support side for receiving liquid products and retaining liquid about the biofilm support side. A feed gas chamber receives the feed gas and communicates the feed gas with the outer face of the liquid impermeable layer at sufficient pressure to maintain a gas phase in the pores of the microporous layer. A liquid recovery conduit provides fluid communication with the liquid retention chamber for recovering the liquid product from the bioreactor membrane system.

Another broad embodiment of this invention is bioreactor membrane system for converting a feed gas containing at least one of CO or a mixture of $CO_2$ and $H_2$ to a liquid product under anaerobic conditions. The system includes a bio-support membrane having a microporous layer and a liquid impermeable layer with one side of each layer defining opposing inner faces and the opposite side of each layer defining an outer face. The outer face of the microporous layer provides a biofilm support side for maintaining a biofilm containing a microorganism that produces the liquid product. The outer face of the liquid impermeable layer provides a gas contacting side in contact with the feed gas for transferring said feed gas across the liquid impermeable layer. A liquid retention chamber establishes fluid communication with the biofilm support side for receiving liquid products and retaining liquid about the biofilm support side. A feed gas chamber receives the feed gas and communicates the feed gas with the outer face of the liquid impermeable layer. A liquid recovery conduit in fluid communication with the liquid retention chamber recovers the liquid product from the bioreactor membrane system.

An additional embodiment of this invention uses a liquid retention chamber in fluid communication with the biofilm support side of the membrane that retains liquid having a redox potential of less than −200 mV in contact with the biofilm.

A microporous surface of the membrane concurrently serves as the support upon which the fermenting cells grow as a biofilm and are thus retained in a concentrated layer.

An additional embodiment of the instant invention includes the supply of dissolved syngas in the liquid phase to the side of the biofilm in contact with that phase. This allows dissolved gas substrate to penetrate from both sides of the biofilm and maintains the concentration within the biofilm at higher levels allowing improved reaction rates compared to just supplying the syngas via the membrane alone. This may be accomplished by pumping a liquid stream where the gases are predissolved into the liquid or by pumping a mixture of liquid containing the syngas present as small bubbles using fine bubble diffusers, jet diffusers or other similar equipment commonly used to transfer gas into liquids. The potential added advantage of using the combined gas and liquid stream is that the additional shear produced by the gas/liquid mixture may be beneficial in controlling the thickness of the biofilm.

The advantage of pre-dissolution of the syngas is that very little, if any, of the gas is lost from the system so utilization efficiency is maximized.

Another embodiment of this invention includes the preferential removal of the carbon dioxide ($CO_2$) gas that is formed in the bioconversion process from the syngas using a membrane that selectively permeates $CO_2$ and then returning the syngas enriched in CO and $H_2$ to the bioreactor.

DETAILED DESCRIPTION OF THE INVENTION

Figure 1:
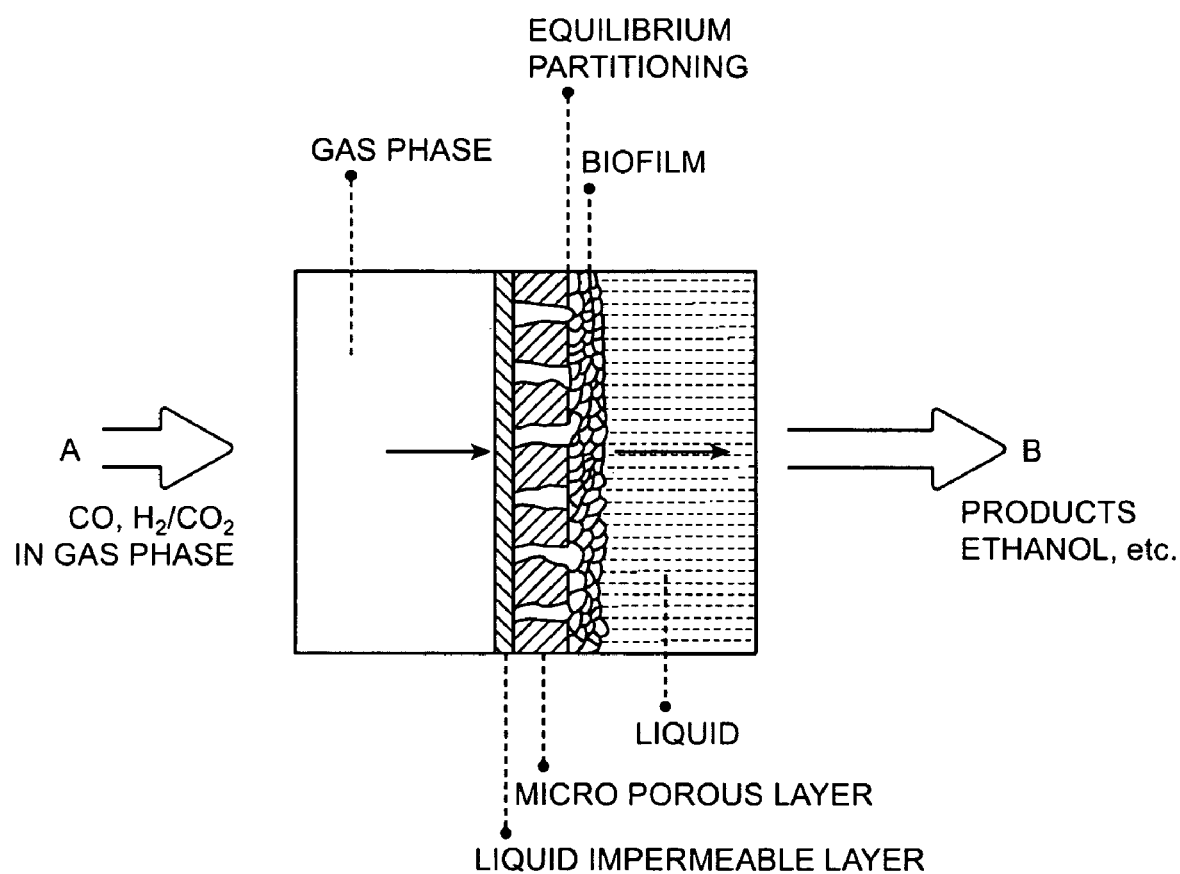
FIG. 1 is a schematic drawing showing gas diffusing through a membrane into a liquid and the relative position of microporous layer and liquid impermeable layer of the membrane.

The system and process of this invention may be used for a broad range of bioconversions. Suitable applications include any in which normally gaseous materials pass as feed to microorganisms that populate a surface of a membrane suspended in a liquid medium. The surface of the membrane may retain many types of microorganisms which can produce various liquid soluble products. This invention finds particular suitability in the production of liquid using microorganisms under anaerobic conditions especially those for producing liquid products from syngas components.

Bioconversions of CO and $H_2/CO_2$ to acetic acid, ethanol and other products are well known. For example, in a recent book concise description of biochemical pathways and energetics of such bioconversions have been summarized by Das, A. and L. G. Ljungdahl, *Electron Transport System in Acetogens* and by Drake, H. L. and K. Kusel, *Diverse Physiologic Potential of Acetogens*, appearing respectively as Chapters 14 and 13 of Biochemistry and Physiology of Anaerobic Bacteria, L. G. Ljungdahl eds., Springer (2003). Any suitable microorganisms that have the ability to convert the syngas components: CO, $H_2$, $CO_2$ individually or in combination with each other or with other components that are typically present in syngas may be utilized. Suitable microorganisms and/or growth conditions may include those disclosed in U.S. patent application Ser. No. 11/441,392, filed May 25, 2006, entitled "Indirect Or Direct Fermentation of Biomass to Fuel Alcohol," which discloses a biologically pure culture of the microorganism *Clostridium carboxidivorans* having all of the identifying characteristics of ATCC no. BAA-624; and U.S. patent application Ser. No. 11/514,385 filed Aug. 31, 2006 entitled "Isolation and Characterization of Novel Clostridial Species," which discloses a biologically pure culture of the microorganism *Clostridium ragsdalei* having all of the identifying characteristics of ATCC No. BAA-622; both of which are incorporated herein by reference in their entirety. *Clostridium carboxidivorans* may be used, for example, to ferment syngas to ethanol and/or n-butanol and/or acetic acid. *Clostridium ragsdalei* may be used, for example, to ferment syngas to ethanol.

Suitable microorganisms and growth conditions include the anaerobic bacteria *Butyribacterium methylotrophicum*, having the identifying characteristics of ATCC 33266 which can be adapted to CO and used and this will enable the production of n-butanol as well as butyric acid as taught in the references: "Evidence for Production of n-Butanol from Carbon Monoxide by *Butyribacterium methylotrophicum*," Journal of Fermentation and Bioengineering, vol. 72, 1991, p. 58-60; "Production of butanol and ethanol from synthesis gas via fermentation," FUEL, vol. 70, May 1991, p. 615-619. Other suitable microorganisms include *Clostridium Ljungdahlii*, with strains having the identifying characteristics of ATCC 49587 (U.S. Pat. No. 5,173,429) and ATCC 55988 and 55989 (U.S. Pat. No. 6,136,577) and this will enable the production of ethanol as well as acetic acid. All of these references are incorporated herein in their entirety.

The microorganisms found most suitable thus far for this invention require anaerobic growth conditions. Therefore the system will employ suitable control and sealing methods to limit the introduction of oxygen into the system. Since the organisms reside principally in contact with the liquid volume of the retention chamber the system maintains a suitable redox potential in the liquid and this chamber may be monitored to insure anaerobic conditions. Anaerobic conditions in the retained liquid volume are usually defined as having a redox potential of less than −200 mV and preferably a redox potential in the range of from −300 to −500 mV. To further minimize exposure of the microorganisms to oxygen the feed gas will preferably have an oxygen concentration of less than 1000 ppm, more preferably less than 100 ppm, and even more preferably less than 10 ppm.

The instant invention uses a combination of a microporous membrane layer and a non-porous membrane layer to transfer gases into direct gas phase contact with microorganisms that consume the gas in the production of liquid products. Keeping the gas pressure on the gas phase side of the membrane above the pressure on the liquid phase side can enhance the direct gas phase contact of feed gas with the microorganism. Relatively higher gas pressure can create or enlarge the gas pocket within the porous layer of the membrane and prevent wetting of the microorganism-gas interface.

In the specific case of ethanol production from syngas, CO and/or $CO_2$ and $H_2$ in the gas contact the microorganisms that transform them into ethanol and other soluble products. The microporous membrane layer can concurrently serve as the support upon which the fermenting cells grow as a biofilm and are thus retained in a concentrated layer. The result is a highly efficient and economical transfer of the syngas at essentially 100% dissolution and utilization that overcomes limitations of other fermentation methods and fermenter configurations. The syngas diffuses through the membrane from the gas side and into the biofilm where it is transformed by the microbes to the soluble product of interest. Liquid passes through the liquid side of the membranes via pumping, stirring or similar means to remove the ethanol and other soluble products formed; the products are recovered via a variety of suitable methods.

The membrane for use in the system and process will include a microporous layer and a liquid impermeable layer. Suitable membranes may contain only the two necessary layers or may include additional functional or non-functional layers. In its simplest arrangement the membrane will retain the two layers against each other, the outer surface of the liquid impermeable layer contacts the gas phase directly while the outer surface of the microporous layer retains the biofilm.

Both membrane layers act in concert to prevent or drastically inhibit the deposition of hydrophilic fluids into membranes pores that open against the microorganisms. Maintaining a small pressure gradient in the membrane pores between the liquid impermeable layer keeps liquid displaced from the pores. Ordinarily the biofilm forms at the outer surface of this microporous layer but will not penetrate into pores and consumes the provided gas at a balanced rate.

Some arrangements may use a liquid impermeable layer that allows the preferential transfer of $H_2$ and CO over $CO_2$. This type of operation enables a bioreactor system to preferentially enrich the gas composition in favor of $H_2$ and CO for consumption by the biofilm.

One form of the liquid impermeable layer consists of a coating applied to the surface of the microporous layer. Effective coatings of this type will limit gas transfer rates across the coating to an acceptable range and may have a thickness of from 1 to 2 microns. Feasible methods of coating application include solvent or emulsion deposition on the inside or outside of the microporous layer or plasma deposition on the outside layer.

Coating the surface of a microporous membrane with a thin layer of silicone provides an effective membrane for this invention. The excellent gas permeability of silicone makes it particularly suitable for this application. Eash et al. (ASAIO Journal, 50(5): 491-497, 2004) established the usefulness of silicone in the development of artificial lungs and provides a good summary of information. Alternatively, the surface coating can be a thin layer of poly[1-(trimethylsilyl)-1-propyne] (PTMSP), which is known to have very high permeability for gases (See Polymer Handbook, James E. Mark, ed, Oxford University Press (1999).)

Microporous membranes made from polymers or ceramics have been recently developed and commercialized for wastewater treatment and purification applications. Some variations of these have also been developed for aeration or oxygenation of liquids. Typically these membranes are made from hydrophobic polymers such as polyethylene or polypropylene which are processed to create a fine porous structure in the polymer film. Many commercial organizations supply such membranes primarily in two important geometries—hollow fiber and flat sheets. These can then be made into modules by appropriate potting and fitting and these modules have very high surface area of pores in small volumes.

Suitable hydrophobic microporous hollow fiber membranes have been used for degassing applications to remove oxygen, carbon dioxide, and other gases from water and other liquids. An example of commercial membrane modules for such applications is the Liqui-Cel® membrane contactor from Membrana (Charlotte, N.C.), containing the polypropylene (PP) X40 or X50 hollow fibers. CELGARD® microporous PP hollow fiber membrane, containing the X30 fibers, is also available from Membrana for oxygenation applications. Liqui-Cel® membrane modules suitable for large scale industrial applications have large membrane surface areas (e.g., 220 m² active membrane surface area for Liqui-Cel® Industrial 14×28). Some characteristics of these fibers are given in the Table 1 below.

TABLE 1

|  | X30 | X40 | X50 |
|---|---|---|---|
| Porosity (nominal) | 40% | 25% | 40% |
| Pore Size | 0.03 μm | 0.04 μm | 0.04 μm |
| Internal Diameter | 240 μm | 200 μm | 220 μm |
| Outer Diameter | 300 μm | 300 μm | 300 μm |
| Wall Thickness | 30 μm | 50 μm | 40 μm |

A microporous PP hollow fiber membrane product (CellGas® module) is available from Spectrum Laboratories (Rancho Dominguez, Calif.) for gentle oxygenation of bioreactors without excessive shear to the microbial or cell cultures. This PP hollow fiber is hydrophobic, with a nominal pore size of 0.05 μm and a fiber inner diameter of 0.2 mm.

For the use of hydrophobic microporous membranes for afore-mentioned applications, it is necessary to properly manage the pressure difference across the membrane to avoid formation of bubbles in the liquid. If the pressure difference is greater than a critical pressure, the value of which depends on properties of the liquid and the membrane, liquid can enter the pore ("wetting") and the gas transfer rate is significantly impeded.

To prevent wetting of pores during operations, some composite membranes have been developed by the membrane suppliers. The SuperPhobic® membrane contactor from Membrana keeps the gas phase and liquid phase independent by placing a physical barrier in the form of a gas-permeable non-porous membrane layer on the membrane surface that contacts the process liquid. The SuperPhobic® 4×28 module contains 21.7 m² of membrane surface area. Another composite hollow fiber membrane with an ultra-thin nonporous membrane sandwiched between two porous membranes is available from Mitsubishi Rayon (Model MHF3504) in the form of composite hollow fibers having at 34 m² membrane area per module. Non-porous (dense) polymeric membranes have been used commercially for various gas separation applications. These membranes separate gases by the selective permeation across the membrane wall. The solubility in the membrane material and the rate of diffusion through the molecular free volume in the membrane wall determine its permeation rate for each gas. Gases that exhibit high solubility in the membranes and gasses that are small in molecular size permeate faster than larger, less soluble gases. Therefore, the desired gas separation is achieved by using membranes with suitable selectivity in conjunction with appropriate operating conditions. For example, Hydrogen Membranes from Medal (Newport, Del.) are used in recovery or purification of hydrogen with preferential permeation of hydrogen and $CO_2$. Medal also provides membranes for $CO_2$ removal with preferential permeation of $CO_2$.

Microporous membranes have been used widely in membrane bioreactors for wastewater treatment. Installations are mostly in the submerged membrane configuration using hollow fiber or flat sheet membranes for wastewater treatment. The structure and module configuration of these membranes may prove particularly useful for the systems of this invention. The membranes are typically made of poly(vinylidene fluoride) (PVDF), polyethylene (PE), PP, poly(vinyl chloride) (PVC), or other polymeric materials. The typical pore size is in the range of 0.03 to 0.4 μm. The typical hollow fiber outer diameter is 0.5 to 2.8 mm and inner diameter 0.3 to 1.2 mm. In these submerged membrane configurations, wastewater containing contaminants are fed into a tank and treated water is filtered through the membrane with a suction pressure applied to the filtrate side (the lumen side of the hollow fiber or the center of the flat plate) of the membrane. Typically the tank retains multiple membrane modules submerged without an individual housing. There are a number of commercial suppliers of membranes for submerged membrane bioreactors in wastewater treatment, each with some distinct features in membrane geometry and module design as described below. These membrane geometries and module designs can be suitable for the instant invention and are incorporated herein.

A hollow fiber membrane SteraporeSUN™, available from Mistubishi Rayon (Tokyo, Japan), is made of PE with modified hydrophilic membrane surface. The hollow fiber has a nominal pore size of 0.4 µm and a fiber outer diameter of 0.54 mm. A SteraporeSUN™ membrane unit Model SUN21034LAN has a total membrane surface area of 210 m$^2$, containing 70 membrane elements Model SUR334LA, each with 3 m$^2$ membrane area.

Another hollow fiber membrane SteraporeSADF™ is available from Mitsubishi Rayon. This membrane is made of PVDF with a nominal pore size of 0.4 µm and a fiber outer diameter of 2.8 mm. Each SteraporeSADF™ membrane element Model SADF2590 contains 25 m$^2$ membrane surface area, and each StreraporeSADF™ membrane unit Model SA50090APE06 containing 20 SADF2590 membrane elements has a total membrane surface area of 500 m$^2$.

Other commercial microporous hollow fiber membranes used for membrane bioreactors include but are not limited to the Zenon ZeeWeed® membranes from GE Water & Process Technologies (Oakville, Ontario, Canada), the Puron® membranes from Koch Membrane Systems (Wilmington, Mass.), and the MemJet® membranes from Siemens Water Technologies (Warrendale, Pa.).

A gas transfer membrane module Model MHF0504 MBFT is available from Mitsubishi Rayon Engineering (Tokyo, Japan). The module contains composite hollow fiber membranes with a triple-layer construction, consisting of a thin liquid impermeable layer sandwiched between two porous layers. In this construction the outer microporous layer provides the biofilm support side. The inner microporous layer can provide structural support to the membrane. Saturation of the inner microporous layer can interfere with gas transfer so the system may benefit from the feed gas undergoing drying to reduce the accumulation of condensation within the inner microporous layer.

Kubota Corporation (Tokyo, Japan) markets submerged membrane systems for membrane bioreactors. These membranes are of the flat-plate configuration and made of PVC with a pore size of 0.4 µm. Each membrane cartridge has 0.8 m$^2$ membrane surface area, and a Model EK-400 membrane unit, containing 400 membrane cartridges, has a total membrane area of 320 m$^2$.

The feed gas flows through the gas chamber of the membrane unit continuously or intermittently. The feed gas pressure is in the range of 1 to 1000 psia, preferably 5 to 400 psia, and most preferably 10 to 200 psia. Operating at higher gas pressures has the advantage of increasing the solubilities of gases in the liquid and potentially increasing the rates of gas transfer and bioconversion. The differential pressure between the liquid and gas phases is managed in a manner that the membrane integrity is not compromised (e.g., the burst strength of the membrane is not exceeded) and the desired gas-liquid interface phase is maintained.

In this invention, a bio-support membrane suitable for permeation of at least one of CO or a mixture of $H_2$ and $CO_2$ provides the separation between a feed gas and a liquid phase. FIG. 1 shows more detail of the membrane configuration and interface in the operation of a representative bio-reactor system. FIG. 1 depicts syngas stream A flowing to the gas feed side of the membrane in gas phase maintained in a chamber on the gas contact side of the membrane. The syngas components freely diffuse through the liquid impermeable layer then into the gas space inside the pores of the microporous layer in contact with the biofilm. The anaerobic acetogenic bacteria, *Clostridium ragsdaeli*, having all of the identifying characteristics of ATCC No. BAA-622, is maintained in a fermentation media. The fermentation media is circulated through a chamber on the opposite side of the membrane that maintains a liquid volume in contact with the liquid side of the membrane. Suitable microbial cells are present as bio-film on the liquid-contacting side of the membrane surface, converting at least one of CO or $H_2/CO_2$ in the feed gas to desirable products. Since the membrane pores are much smaller than the width of the microorganisms they preferentially stay on the membrane surface to convert CO and $H_2/CO_2$ to gain metabolic energy, grow and form a biofilm on the membrane surface. A stream B withdraws the liquid phase components from a liquid volume retained about the outer surface of the biofilm.

As readily appreciated from the diagrams of FIG. 1, control of the relative pressure between the gas phase supplied by input A and the liquid phase withdrawn by effluent B can restrict the presence of liquid in the pores of the microporous membrane layer. Maintaining a small positive pressure gradient between the gas phase and the liquid (aqueous) phase establishes a "gas pocket" inside the pores of the microporous layer to prevent liquid seepage therein. The required pressure differential varies with a variety of factors including the composition of the membrane layers, thickness of the membrane layers, liquid phase and gas phase compositions, gas transfer rates and gas consumption rates. For most applications the pressure differential will range from 0.1 to 50 psi.

Figure 2:
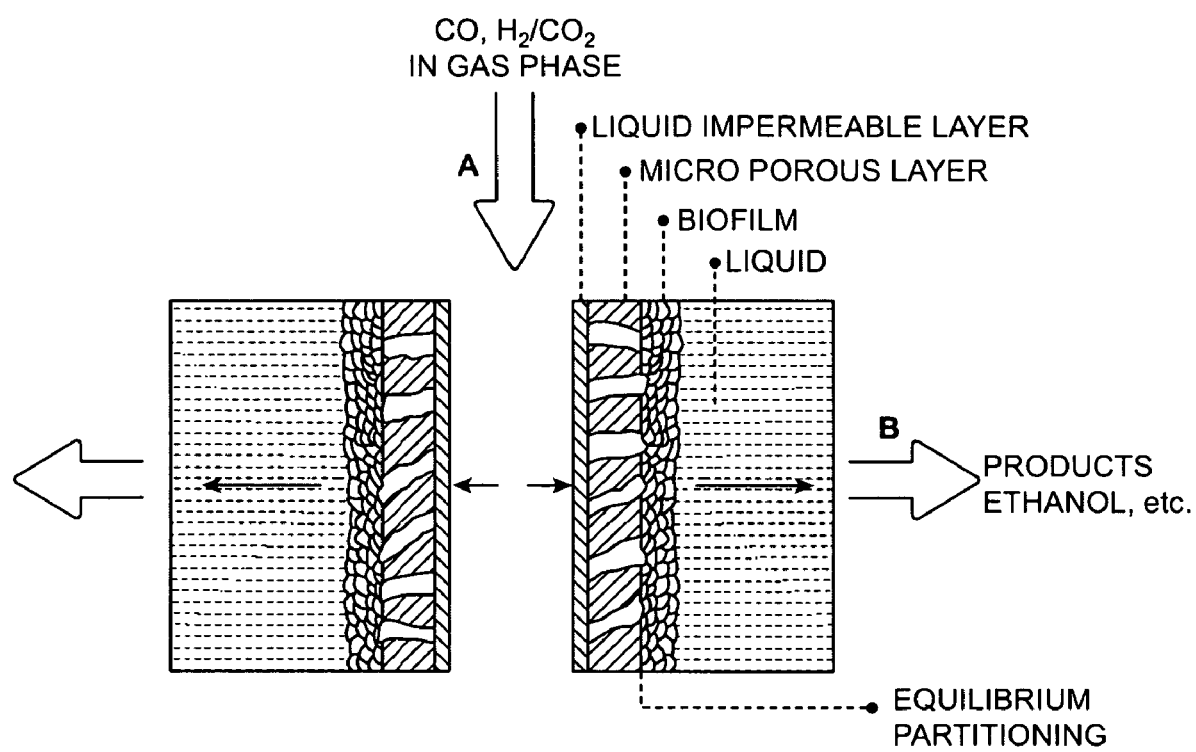
FIG. 2 is a schematic drawing showing a central passage delivering gas to two parallel membrane walls with a liquid phase to the outside of each wall.

FIG. 2 depicts a generalized view of a typical flow arrangement for efficient use of space in a membrane system. Syngas components enter the system as gas stream A, which flows into a central space between two membrane walls. The gas phase contact surfaces of the liquid impermeable layer on opposing membrane walls to form a distribution chamber for receiving gas from stream A. Gas permeates simultaneous through, in this case, the liquid impermeable layer and microporous layer of membrane for consumption by the microbes in the biofilm layers that adhere to the outer walls of the two opposing membranes. In this manner each gas channel serves multiple membrane surfaces and the stream B of liquid products is delivered from multiple membrane walls. The arrangement of FIG. 2 can use a flat sheet configuration and be particularly useful for good flow control and distribution on the liquid side that may be necessary for biofilm thickness control.

Figure 3:
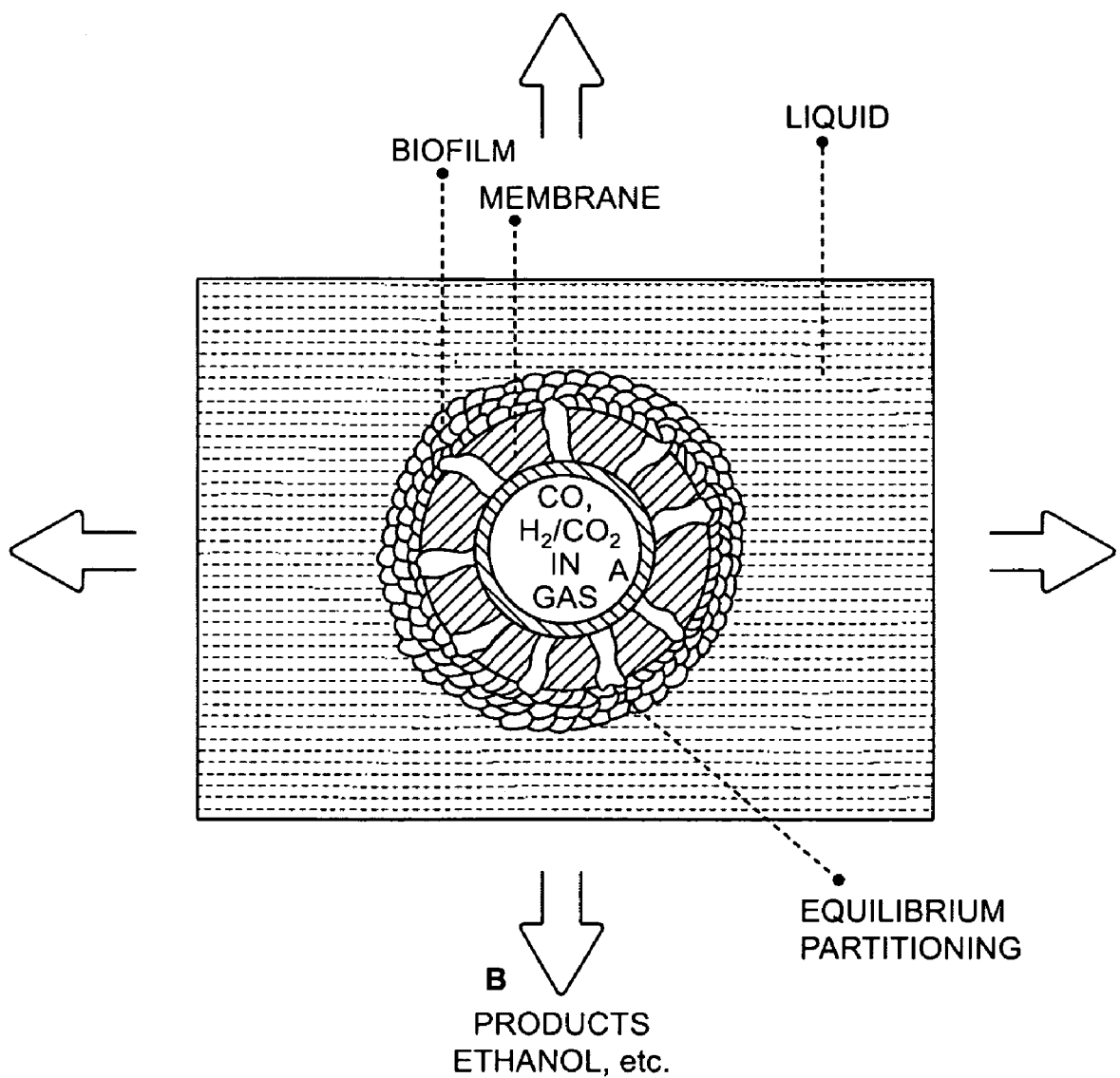
FIG. 3 is a schematic drawing showing the interior passage of FIG. 2 enclosed by the interior surface of the membrane in tubular form with liquid retained around the membrane circumference.

FIG. 3 shows the special case of FIG. 2 wherein the opposite wall of the central distribution chamber wrap around in continuous form to provide a tubular membrane. In this case gas stream A enters the lumen of the membrane and streams B of liquid products flow away from the outer walls in all directions. Hollow fibers are particularly useful for such bioreactor configurations.

Figure 4:
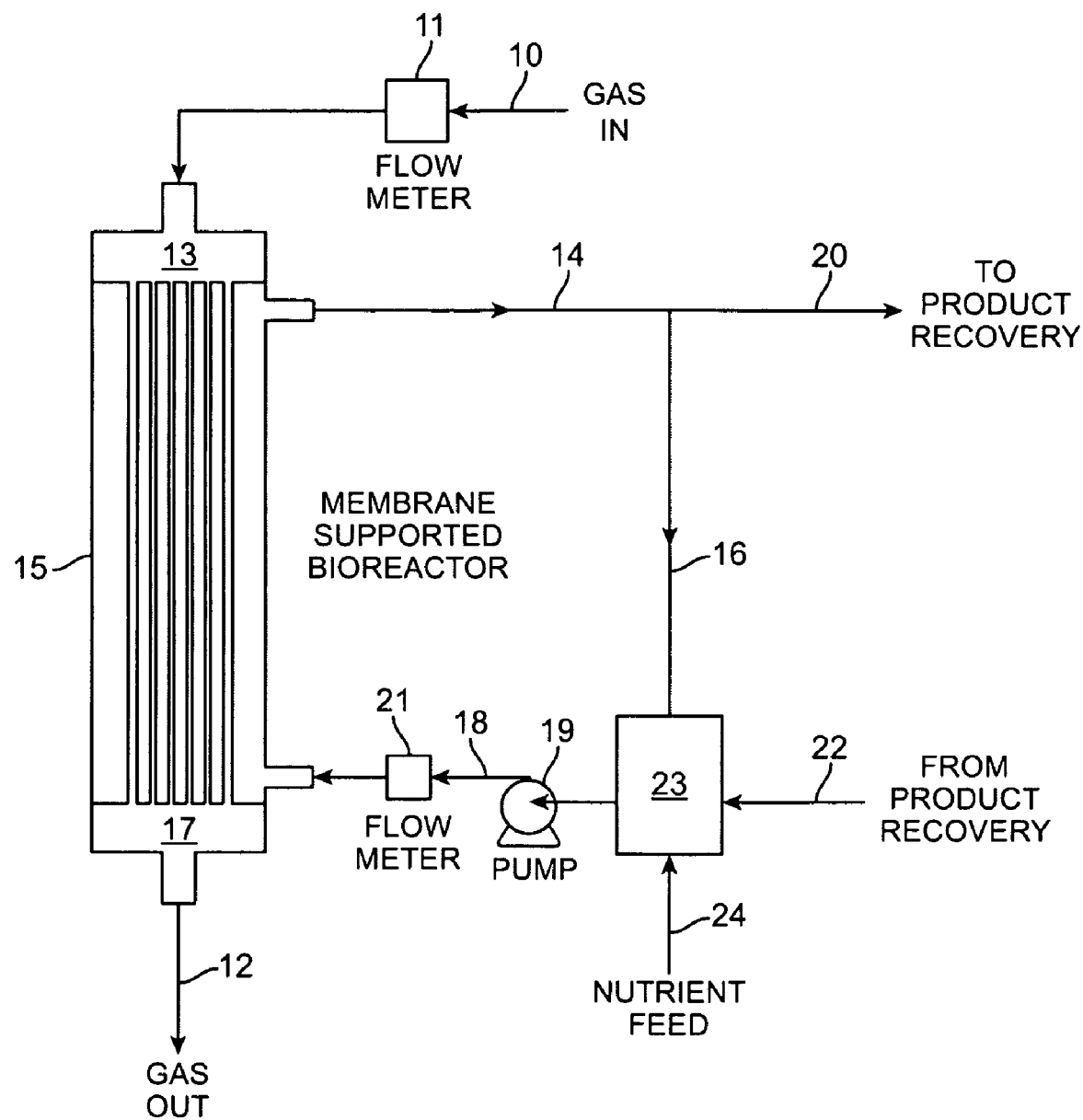
FIG. 4 is a schematic drawing showing a bioreactor system with gas and liquid circulation.

FIG. 4 illustrates a specific configuration of one embodiment of this invention. A gas supply conduit delivers a feed gas Stream 10 containing CO, $H_2$, and $CO_2$ at a rate recorded by a flow meter 11. A feed gas distribution chamber 13 receives the feed gas stream and distributes the feed to the lumens of tubular membranes in a membrane unit 15 that provides a membrane supported bioreactor. A collection chamber 17 collects a portion of the feed gas that exits the lumens and an exhaust gas stream 12 from chamber 17 exits the membrane unit.

A membrane vessel surrounds the outside of the tubular membrane elements in the membrane supported bioreactor and retains a liquid for growth and maintenance of a biofilm layer on the outer surface of the membrane. A re-circulating liquid loop, consisting of Streams 14, 16, and 18 re-circulates liquid through the vessel. Liquid flows from the vessel through lines 14 and 16 while line 20 withdraws liquid and takes it to product recovery to recover liquid products. The product recovery step removes the desirable product from Stream 20, while leaving substantial amounts of water and residual nutrients in the treated stream, part of which is returned to the bioreactor system via line 22. A nutrient feed is added via line 24 is added, as needed, to compensate for the amount of water removed and to replenish nutrients. Chamber 23 provides the means of temperature and pH controls for the liquid, which contains nutrients needed to sustain the activity of the microbial cells. The liquid in Chamber 23 is stirred to provide adequate mixing and sparged with a suitable gas, if necessary, to maintain a suitable gaseous environment. Line 18 returns the remaining liquid from line 16 as well as Streams 22 and 24 to the membrane vessel via pump 19 at rate recorded by flow meter 21.

The flow rates of Streams 18 and 14, recirculated through the membrane unit, are selected so that there is no significant liquid boundary layer that impedes mass transfer near the liquid-facing side of the membrane and there is no excessive shear that may severely limit the attachment of cells and formation of the biofilm on the membrane surface. The superficial linear velocity of the liquid tangential to the membrane should be in the range of 0.01 to 100 cm/s, preferably 0.05 to 20 cm/s, and most preferably 0.2 to 5.0 cm/s. In addition to the liquid linear velocity, the biofilm thickness can be controlled by other means to create shear on the liquid-biofilm interface, including scouring of the external membrane surface with gas bubbles and free movement of the hollow fibers. Also, operating conditions that affect the metabolic activity of the microbial cells and the mass transfer rates of gases and nutrients can be manipulated to control the biofilm thickness. The biofilm thickness in the instant invention is in the range of 5-500 μm, preferably 5-200 μm.

Depending on the nature of the desired product, there are a number of technologies that can be used for product recovery. For example, distillation, dephlegmation, pervaporation and liquid-liquid extraction can be used for the recovery of ethanol and n-butanol, whereas electrodialysis and ion-exchange can be used for the recovery of acetate, butyrate, and other ionic products.

In all the depicted arrangements, the CO an $H_2$ from the syngas are utilized and a gradient for their transport from the gas feed side is created due to biochemical reaction on the membrane liquid interface. This reaction creates liquid fuel or chemicals such as ethanol and acetic acid which diffuse into the liquid and are removed via circulation of the liquid past the biofilm. Thus the very large surface areas of the membrane pores are usable for gas transfer to the biofilm and the product is recovered from the liquid side. Furthermore, the reaction rate, gas concentration gradient and the thickness of the biofilm can be maintained in equilibrium because the microorganisms in the biofilm will maintain itself only up to the layer where the gas is available.

The membranes can be configured into typical modules as shown as an example in FIG. 4 for hollow fibers. The gas flows in the fine fibers that are bundled and potted inside a cylindrical shell or vessel through which the liquid is distributed and circulated. Very high surface areas in the range of 1000 m2 to 5000 m2 per m3 can be achieved in such modules.

The bioreactor modules can be operated multi-stage operation of fermentation using the modules in counter-current, co-current or a combination thereof mode between the gas and the liquid. In the example as shown in FIG. 4 a counter current operation is depicted.

During the bioconversion excess $CO_2$ is generated and this gas can diffuse back and dilute out the concentrations of CO and $H_2$ in the feed gas and thus reduce their mass transfer rates. Other types of membranes that preferentially permeate $CO_2$ over CO and $H_2$ can be used in the multi stage configuration as shown as an example in FIG. 5 where, using a membrane that selectively permeates $CO_2$ and then returning the syngas enriched in CO and $H_2$ to the bioreactor can be achieved.

Figure 5:
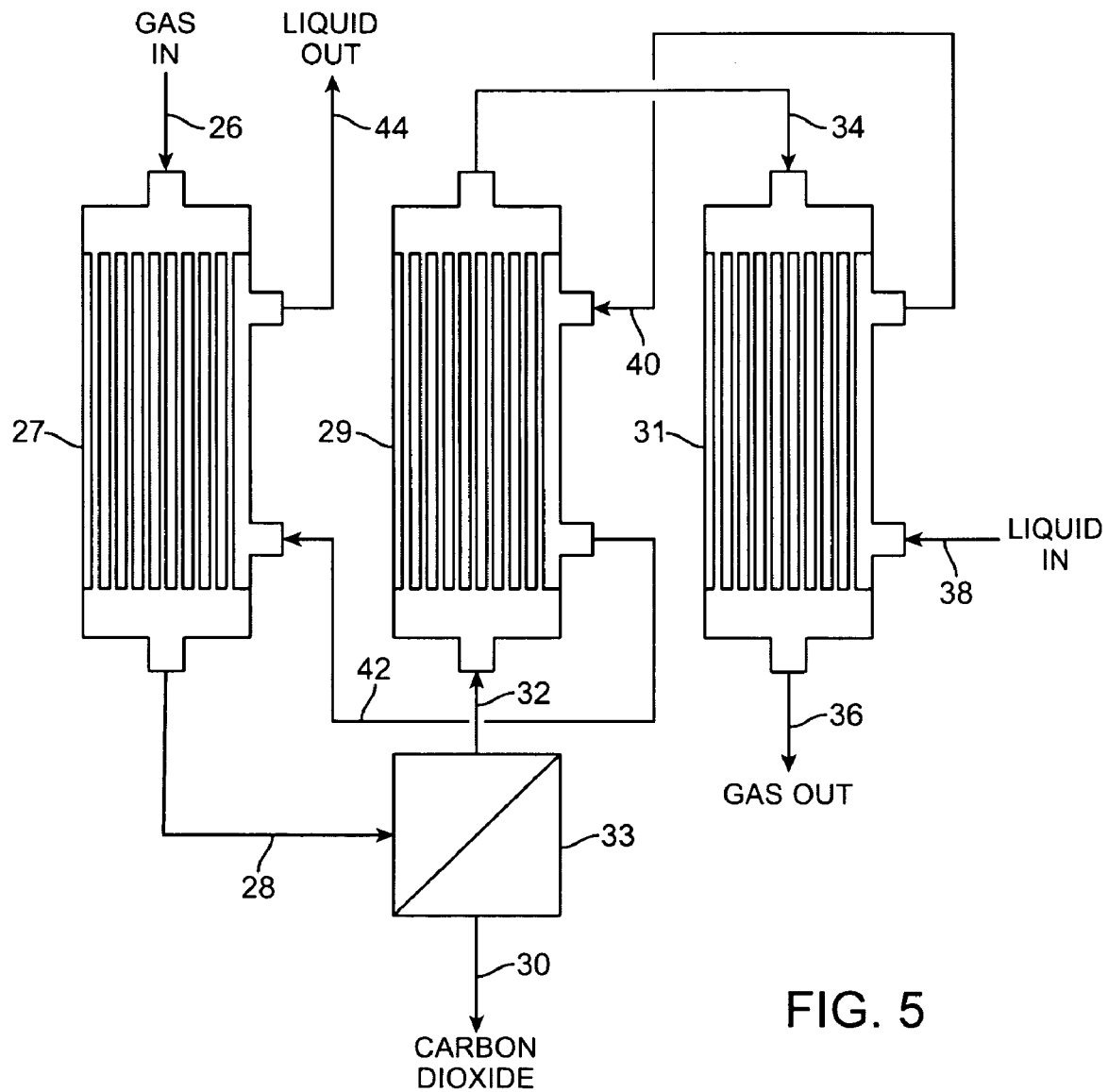
FIG. 5 is a schematic drawing showing a bioreactor system with multiple bioreactors arranged in series having intermediate carbon dioxide removal.

FIG. 5 depicts a system where the entering feed gas flows into bioreactor 27 via line 26 and serially through bioreactors 29 and 31 via lines 28, 32 and 34. At the same time liquid that contacts the biofilm layers enters the system via line 38 and flows countercurrently, with respect to the gas flow, through bioreactors 31, 29 and 27 via lines 40 and 42. Liquid products are recovered from the liquid flowing out of line 44 and gas stream is withdrawn from the system via line 36. Separation unit 33 provides the stream of line 28 with intermediate removal of $CO_2$ from the system via any suitable device or process such as a membrane or extraction step. Interconnecting lines 32 and 34 also provide the function of establishing continuous communication through all of the lumens of the different bioreactors so that any combined collection and distribution chambers provide a continuous flow path.

Example 1

The membrane permeance of syngas components was measured for Membrane A, a gas transfer membrane module Model MHF0504MBFT from Mitsubishi Rayon Engineering (Tokyo, Japan). The module contains composite hollow fiber membranes with a triple-layer construction, consisting of a thin liquid impermeable layer sandwiched between two porous layers. The fiber outer diameter is approximately 280 μm and inner diameter approximately 200 μm. The nominal membrane surface area in the module was 0.6 $m^2$. A source of syngas, containing 39.0% CO, 33.5% $H_2$, 23.1% $CO_2$ and 4.4% $N_2$, was connected to the lumen inlet of the module, while the lumen outlet was closed with a shut-off valve. The syngas feed pressure was maintained at a desired level, and the feed flow rate was measured with a calibrated flow meter. Syngas components passed through the membrane into the shell side of the module, and the permeate flow rate was measured with a bubble flow meter. Pressures at the lumen inlet, lumen outlet and shell-side outlet were measured with pressure gauges. Gas samples were taken at the lumen inlet, lumen outlet and permeate and analyzed for their compositions using a gas chromatograph equipped with a thermal conductivity detector. The measurement was performed at three different syngas feed pressures at 1, 3, and 5 psi. The membrane permeance for each syngas component was then calculated. The values were 0.020 L/min/$m^2$/psi for CO, 0.069 L/min/$m^2$/psi for $H_2$, 0.091 L/min/$m^2$/psi for $CO_2$.

Example 2

A membrane module measuring 4" diameter and 40" length and containing a gas transfer membrane described in Example 1 was used as a membrane supported bioreactor for the conversion of carbon monoxide and hydrogen into ethanol. The active membrane surface area of the module was 17.1 $m^2$, based on fiber outer diameter. The packing density of the module, calculated as the volume occupied by the fibers divided by the internal volume of the module, was 16%. The membrane module was housed in constant temperature chamber at 37° C. and connected to a 10-liter BIOSTAT Bplus Fermentor from Sartorius AG (Goettingen, Germany). The fermentor initially contained 8 liters of the fermentation medium, which was agitated at 300 rpm and maintained at 37° C. The fermentor was maintained under anaerobic conditions. The fresh fermentation medium contained the components listed in Tables 2 & 3(a)-(d). Initially, at t=0 hr the fermentor was operated in the batch mode without connecting to the membrane module and inoculated with 1000 ml of an active culture of Clostridium ragsdalei ATCC No. BAA-622. The fermentor was sparged with syngas at 0.4 std liter/min. The syngas contained approximately 28.5% CO, 24.5% $H_2$, and 38.5% $CO_2$. The fermentation pH was controlled at pH 5.9 in the first 24 hours by addition of 1 N NaOH to favor cell growth and then allowed to drop without control until it reached pH 5.2.

After 32 hours, the fermentor was connected with the membrane module. The fermentor agitation was reduced to 100 rpm. Syngas sparging to the fermentor was stopped and syngas was fed to the lumen of the fibers at 0.5 std liter/min initially and gradually increased to 3 std liter/min over the duration of the run. The gas pressure in the membrane module was at 2.5 psig initially and later adjusted over the range of 0 to 15 psig. The effluent gas from the membrane module was directed to the headspace of the fermentor and exited the fermentor through a condenser and a sterile gas filter. The fermentation medium was pumped from the fermentor, flowed through the shell side of the membrane module, and returned to the fermentor. The flow rate of this re-circulating medium varied between 1.2 and 6.0 liter/min during the course of the run, and the pressure at the outlet of the membrane module was maintained at 0 to 15.5 psig by using a back-pressure regulator. The system remained in the batch mode for 106 hours to establish the attachment of the microbial cells on the membrane surface. Then, the system was switched to continuous operation with continuous withdrawal of the product-containing fermentation broth and replenish of fresh medium, with a liquid residence time of about 48 hours. With the continuous operation, suspended cells in the fermentation broth were gradually removed from the bioreactor system, while the biofilm attached on the membrane surface continued to grow until the biofilm reached a thickness equilibrated with the operating conditions. Operating conditions, such as feed gas flow rate, gas pressure, liquid pressure, liquid re-circulation flow rate, and the yeast extract concentration in the fresh medium, were varied over the course of the run. Gas consumption rate was calculated from the compositions of syngas feed and effluent measured by using an on-line process gas mass spectrometer. Samples of the fermentation broth were taken from the fermentor and analyzed for product concentrations using a gas chromatograph. The operating conditions and results at various time points are given in Table 4. In the first 361 hours, the CO & H2 gas consumption rate as well as the ethanol and acetate concentrations increased over time, as the biofilm grew on the membrane surface and the gas and liquid pressures were increased. After t=361 hr, the gas consumption rate and ethanol concentration gradually declined over time. This decline is attributed to pore-wetting of the lumen-facing porous layer of the hollow fiber membranes. The syngas can become saturated with water quickly after entering the membrane module and then over saturated with water as a portion of the syngas is consumed, resulting in condensation of water inside the lumen. In this fermentation run, gas conversion as high as 30% was achieved at about t=360 hr, and condensate flowing out of lumen was observed. Therefore, it was concluded that inner layer pore-wetting had caused the performance decline and that a microporous layer can provides a biofilm support side for maintaining a biofilm containing a microorganism that produces the liquid product while the outer face of the liquid impermeable layer provides a gas contacting side.

TABLE 2

Fermentation Medium Compositions

| Components | Amount per liter |
| --- | --- |
| Mineral solution, See Table 3(a) | 25 ml |
| Trace metal solution, See Table 3(b) | 10 ml |
| Vitamins solution, See Table 3(c) | 10 ml |
| Yeast Extract | 2 or 8 g |
| Adjust pH with NaOH | 6.1 |
| Reducing agent, See Table 3(d) | 2.5 ml |

TABLE 3(a)

Mineral Solution

| Components | Concentration (g/L) |
| --- | --- |
| NaCl | 80 |
| $NH_4Cl$ | 100 |
| KCl | 10 |
| $KH_2PO_4$ | 10 |
| $MgSO_4 \cdot 7H_2O$ | 20 |
| $CaCl_2 \cdot 2H_2O$ | 4 |

TABLE 3(b)

Trace Metals Solution

| Components | Concentration (g/L) |
| --- | --- |
| Nitrilotriacetic acid | 2.0 |
| Adjust the pH to 6.0 with KOH | |
| $MnSO_4 \cdot H_2O$ | 1.0 |
| $Fe(NH_4)_2(SO_4)_2 \cdot 6H_2O$ | 0.8 |
| $CoCl_2 \cdot 6H_2O$ | 0.2 |
| $ZnSO_4 \cdot 7H_2O$ | 1.0 |
| $NiCl_2 \cdot 6H_2O$ | 0.2 |
| $Na_2MoO_4 \cdot 2H_2O$ | 0.02 |
| $Na_2SeO_4$ | 0.1 |
| $Na_2WO_4$ | 0.2 |

TABLE 3(c)

Vitamin Solution

| Components | Concentration (mg/L) |
| --- | --- |
| Pyridoxine•HCl | 10 |
| Thiamine•HCl | 5 |
| Roboflavin | 5 |
| Calcium Pantothenate | 5 |
| Thioctic acid | 5 |
| p-Aminobenzoic acid | 5 |
| Nicotinic acid | 5 |
| Vitamin B12 | 5 |
| Mercaptoethanesulfonic acid | 5 |
| Biotin | 2 |
| Folic acid | 2 |

TABLE 3(d)

| Reducing Agent | |
|---|---|
| Components | Concentration (g/L) |
| Cysteine (free base) | 40 |
| $Na_2S \cdot 9H_2O$ | 40 |

TABLE 4

Operating Conditions and Results of a Continuous Fermentation Run

| Time (hr) | 193 | 265 | 289 | 313 | 361 | 457 | 505 | 759 |
|---|---|---|---|---|---|---|---|---|
| Gas flow rate (SLPM) | 1.5 | 1.5 | 2.0 | 2.0 | 2.0 | 2.0 | 1.0 | 3.0 |
| Gas pressure (psig) | 2.0 | 2.7 | 5.0 | 10.5 | 15.5 | 15.5 | 12.5 | 5.6 |
| Liquid pressure (psig) | 2.5 | 2.5 | 5.0 | 11.0 | 15.5 | 15.0 | 10.0 | 4.0 |
| Liquid flow rate (L/min) | 1.2 | 1.2 | 2.0 | 2.0 | 2.0 | 6.0 | 2.0 | 3.0 |
| [Yeast extract] (g/L) | 8.0 | 8.0 | 8.0 | 2.0 | 2.0 | 8.0 | 8.0 | 8.0 |
| [Ethanol] (g/L) | 6.4 | 8.4 | 9.1 | 10.5 | 13.3 | 7.0 | 6.1 | 0.8 |
| [Acetate] (g/L) | 9.0 | 8.5 | 9.5 | 9.7 | 10.8 | 10.2 | 14.7 | 17.0 |
| CO & $H_2$ consumption rate (mmol/min) | 8.6 | 8.8 | 10.7 | 12.3 | 14.5 | 11.8 | 5.9 | 6.7 |

The invention claimed is:

1. A bioconversion process for converting a feed gas comprising at least one of CO or a mixture of $CO_2$ and $H_2$ to a liquid product, said process comprising:
   a) providing a membrane comprising at least two layers and having a microporous layer and a liquid impermeable layer with one side of each layer defining opposing inner faces and the opposite side of each layer defining an outer face, wherein the outer face of the microporous layer provides a biofilm support surface and the outer face of the liquid impermeable layer provides a gas contacting side in contact with the feed gas for transferring said feed gas across the liquid impermeable layer to the microporous layer and across the microporous layer to the biofilm support surface;
   b) passing the feed gas through the membrane starting from the liquid impermeable layer and ending at the biofilm support surface;
   c) maintaining the outer surface of the microporous layer in a liquid and supporting and growing a biofilm comprising anaerobic microorganisms on the microporous layer;
   d) converting the feed gas to liquid products by contact with the microorganisms;
   e) maintaining the feed gas at sufficient pressure above the pressure of the liquid at the outer face of the microporous layer to retain pockets of gas in pores of the microporous layer and to displace liquid from the pores and prevent liquid from entering the pores; and,
   f) recovering liquid products from the liquid.

2. The process of claim 1 wherein the liquid impermeable layer comprises a silicone coating on a porous substrate and the porous substrate comprises the microporous layer.

3. The process of claim 1 wherein the process operates under anaerobic conditions and the microorganism produces a liquid product comprising at least one of ethanol, n-butanol, acetic acid, butyric acid, and hexanol and wherein the feed gas is synthesis gas having an oxygen concentration of less than 1000 ppm and the liquid in which the outer surface of the microporous layer is maintained has a redox potential of less than −200 mV.

4. The process of claim 1 wherein the liquid impermeable layer comprises a thin layer of poly[1-(trimethylsilyl)-1-propyne].

5. The process of claim 1 wherein the membrane comprises a plurality of hollow fiber membranes and each fiber has micorporous layer that surrounds the liquid impermeable layer.

6. The process of claim 1 wherein the membrane comprises composite hollow fiber membranes with a triple-layer construction, consisting of a thin liquid impermeable layer sandwiched between two microporous layers and the outer microporous layer provides the biofilm support side.

7. The process of claims 1 wherein the feed gas is dried before it passes to the membrane.

8. The process of claim 1 wherein the microorganism comprises a mono-culture or a co-culture of at least one of *Clostridium ragsdalei*, *Butyribacterium methylotrophicum*, and *Clostridium Ljungdahlii*.

* * * * *